US007611855B2

(12) United States Patent
Ohashi et al.

(10) Patent No.: US 7,611,855 B2
(45) Date of Patent: *Nov. 3, 2009

(54) IMMUNOASSAY METHOD AND KIT TO BE USED THEREIN

(75) Inventors: Tatsuya Ohashi, Koriyama (JP); Toshihide Miura, Koriyama (JP); Yoshihiko Igarashi, Mibu (JP); Fumio Nomura, Chiba (JP); Takeshi Tomonaga, Chiba (JP); Katsuhiro Katayama, Koriyama (JP)

(73) Assignee: Nitto Boseki Co., Ltd., Fukushima-Shi (JP)

( * ) Notice: Subject to any disclaimer, the term of this patent is extended or adjusted under 35 U.S.C. 154(b) by 292 days.

This patent is subject to a terminal disclaimer.

(21) Appl. No.: 10/538,912

(22) PCT Filed: Dec. 24, 2003

(86) PCT No.: PCT/JP03/16601

§ 371 (c)(1),
(2), (4) Date: Jun. 13, 2005

(87) PCT Pub. No.: WO2004/059320

PCT Pub. Date: Jul. 15, 2004

(65) Prior Publication Data

US 2006/0115866 A1 Jun. 1, 2006

(30) Foreign Application Priority Data

Dec. 26, 2002 (JP) ............................. 2002-377636
Apr. 28, 2003 (JP) ............................. 2003-123970

(51) Int. Cl.
*G01N 33/543* (2006.01)
*G01N 33/546* (2006.01)
*G01N 33/573* (2006.01)
*C07K 16/40* (2006.01)
*C12P 21/08* (2006.01)
*C12N 5/20* (2006.01)

(52) U.S. Cl. .................. 435/7.4; 435/7.1; 435/7.92; 435/7.93; 435/7.95; 435/21; 435/70.21; 435/452; 435/174; 435/177; 435/338; 435/962; 435/975; 436/518; 436/523; 436/528; 436/534; 436/548; 436/811; 530/388.26; 530/391.1

(58) Field of Classification Search ................. 435/7.1, 435/7.4, 7.92, 7.93, 7.94, 7.95, 21, 70.21, 435/452, 174, 177, 338, 962, 975; 436/518, 436/523, 528, 534, 548, 811; 530/388.26, 530/389.1, 391.1

See application file for complete search history.

(56) References Cited

U.S. PATENT DOCUMENTS

| 4,745,072 | A | | 5/1988 | Ekins et al. ................ 436/500 |
| 4,769,320 | A | * | 9/1988 | Furie et al. ................ 435/7.92 |
| 5,037,764 | A | | 8/1991 | Wilk et al. |
| 5,382,530 | A | * | 1/1995 | Romelli et al. .............. 436/500 |
| 6,010,866 | A | * | 1/2000 | Ollington et al. ............ 435/7.4 |
| 6,190,873 | B1 | * | 2/2001 | Davalian et al. ........... 435/7.93 |
| 6,248,544 | B1 | * | 6/2001 | Halleen et al. .............. 435/7.4 |
| 6,737,278 | B1 | * | 5/2004 | Carlsson et al. ............ 436/518 |
| 7,074,903 | B2 | * | 7/2006 | Ohashi et al. .......... 530/388.26 |

FOREIGN PATENT DOCUMENTS

| EP | 1 359 161 A2 | 5/2003 |
| JP | 60-501674 | 10/1985 |
| JP | 63-30766 | 2/1988 |
| JP | 6-289020 | 10/1994 |
| JP | 10-221341 | 8/1998 |
| JP | 10-337198 | 12/1998 |
| JP | 2001-281222 | 10/2001 |
| JP | 2002-31640 | 1/2002 |
| WO | WO 85/00226 A1 | 1/1985 |
| WO | WO 01/25791 A2 | 4/2001 |

OTHER PUBLICATIONS

Janckila et al., 1997. Characterization of monoclonal antibodies specific to tartrate-resistant acid phosphatase. Hybridoma 16(2): 175-182.*

J.M. Halleen, et al.; "Tartrate-Resistant Acid Phosphatase 5b: A Novel Serum Marker of Bone Resorption;" *Journal of Bone and Mineral Research*; vol. 15; No. 7; Jul. 2000; Cover Sheet, Index and pp. 1337-1345 (12 Sheets.).

(Continued)

*Primary Examiner*—Ann Y. Lam
*Assistant Examiner*—James L Grun
(74) *Attorney, Agent, or Firm*—Kratz, Quintos & Hanson, LLP (57) ABSTRACT

Using two types of antibodies, i.e., a first antibody having a higher affinity for a target substance than for a competitive substance and a second antibody having a higher affinity for the competitive substance than for the target substance, a specimen is treated with these two antibodies. Then, the competitive substance in the specimen first binds to the second antibody and thus the ratio of the target substance to the competitive substance in the specimen is enlarged. As a result, the target substance becomes liable to bind to the first antibody and, in its turn, the reactivity of the target substance is elevated compared with the case of using the first antibody alone. Thus, the target substance in the specimen can be accurately assayed while avoiding the effects of the competitive substance contained in the specimen.

3 Claims, 3 Drawing Sheets

OTHER PUBLICATIONS

A.J. Janckila, et al.' "Tartrate-resistant Acid Phosphatase Isoform 5b as Serum Marker for Osteroclasitc Activity;" *Clinical Chemistry*; vol. 47; No. 1; Jan. 2001; Cover Sheet, Index and pp. 74-80 (11 Sheets.).

P.D. Delmas; "Standardization of Bone Marker Nomenclature;" *Clinical Chemistry*; vol. 47; No. 8; Aug. 2001; Cover page, index and p. 1497 (6 Sheets.).

"*Nichidai-Ishi*;" Vol. 49; No. 9; 1990; Cover Sheets and pp. 904-911 (6 Sheets.), Abstract only.

K.-H.W. Lau, et al.; "Characterization and Assay of Tartrate-Resistant Acid Phosphatase Activity in Serum: Potential Use to Assess Bone Resorption;" *Clinical Chemistry*; vol. 33; No. 4; Apr. 1987; Cover Sheet., index and pp. 458-462; (10 Sheets.).

M.E. Kraenzlin, et al; "Development of an Immunoassay for Human Serum Osteoclastic Tartrate-Resistant Acid Phosphatase;" *Journal of Clinical Endrocrinology and Metabolism*; vol. 71; No. 2; Aug. 1990; Cover Sheet; Index and pp. 442-451. (15 Sheets.).

S.L. Alatalo, et al; "Rapid Screening Method for Osteoclast Differentiation in Vitro That Measures Tartrate-resistant Acid Phosphatase 5b Activity Secreted into the Culture Medium;" *Clinical Chemistry*; vol. 46, No. 11; Nov. 2000; Cover Sheet, Index and pp. 1751-1754 (8 Sheets.).

J.M. Halleen, et al; "Characterization of Serum Tartrate-Resistant Acid Phosphatase and Development of a Direct Two-Site Immunoassay;" *Journal of Bone and Mineral Research*; vol. 13; No. 4; Apr. 1998; Cover page, Index and pp. 683-687. (9 Sheets.).

H. Bull, et al; "Reactivity and assay restriction profiles of monoclonal and polyclonal antibodies to acid phosphatases: a preliminary study;" *Immunology Letters*; vol. 70; No. 3; Dec. 1, 1999; Cover Sheet; Index and pp. 143-149 (9 Sheets.).

J.M. Halleen, et .; "Two-Site Immunoassays for Osteoclastic Tartrate-Resistant Acid Phosphatase Based on Characterization of Six Monoclonal Antibodies;" *Journal of Bone and Mineral Research*; vol. 14; No. 3; Mar. 1999; Cover Sheet, Index and pp. 464-469 (9 Sheets.).

Y.R. Nakasato, et al; "Clinical Significance of Immunoassays for Type-5 Tartrate-resistant Acid Phosphatase;" *Clinical Chemistry*; vol. 45; No. 12; Dec. 1999; Cover Sheet, Index and pp. 2150-2157 (13 Sheets.).

G. Köhler, et al.;"Continuous cultures of fused cells secreting antibody of predefined specificity;" *Nature*; vol. 256; Aug. 7, 1975; Cover Sheet and pp. 495-497 (4 Sheets.).

N. Ulloa et al; "Characterization of Monoclonal Antibodies Against Apolipoproteins A-I and A-II. Epitope Expression in LpA-I and LpA-I:LpA-II Particles"; Hybridoma; Liebert; New York, NY, US. vol. 18, No. 6; Dec. 1, 1999; pp. 513-520, XP009014610.

Supplementary European Search Report dated May 26, 2008.

Chinese Office Action dated May 25, 2007 and English Translation.

* cited by examiner

FIG. 1

RESULTS OF ASSAY USING PROTEIN CHIPS

FIG. 2

RESULT OF ASSAY USING PROTEIN CHIPS

① Trk49 ANTIBODY PROTEIN CHIP  SERUM OF AN ADULT
② Trk49 ANTIBODY PROTEIN CHIP  SERUM OF AN INFANT
③ Trk62 ANTIBODY PROTEIN CHIP  SERUM OF AN ADULT
④ Trk62 ANTIBODY PROTEIN CHIP  SERUM OF AN INFANT
⑤ Trk49 ANTIBODY PROTEIN CHIP  SERUM OF A PATIENT WITH OSTEOPOROSIS BEFORE HORMONE SUBSTITUTION THERAPY
⑥ Trk49 ANTIBODY PROTEIN CHIP  SERUM OF A PATIENT WITH OSTEOPOROSIS AFTER HORMONE SUBSTITUTION THERAPY

FIG. 3

RESULT OF ASSAY BY ELISA METHOD

FIG. 4

RESULT OF ELISA EXPERIMENT BY ADDITION OF LATEX REAGENT

IMMUNOASSAY METHOD AND KIT TO BE USED THEREIN

TECHNICAL FIELD

The present invention relates to an immunoassay method that permits accurate assay of a target substance in a specimen by the use of two types of characteristic antibodies, and a kit to be used in the method. More particularly, the present invention relates to an immunoassay method in which using two types of antibodies, i.e., a first antibody having a higher affinity for a target substance than for a competitive substance and a second antibody having a higher affinity for the competitive substance than for the target substance, a specimen is treated with these two antibodies, whereupon the competitive substance in the specimen first binds to the second antibody and thus the ratio of the target substance to the competitive substance in the specimen is enlarged, so that the target substance becomes liable to bind to the first antibody, and as a result, the reactivity of the target substance is elevated compared with the case of using the first antibody alone, so that the target substance can be accurately assayed; and a kit to be used in this method.

BACKGROUND ART

Various types of substances are present in a specimen containing a target substance to be assayed, and a target substance to be assayed and a substance competitive therewith are present in a certain specimen at the same time in some cases. For example, a large portion of tartrate resistant acid phosphatase (TRACP) in serum is considered acid phosphatase derived from osteoclast and the assay of TRACP is considered useful as an indication for evaluating the function of osteoclast. Thus, TRACP is a substance that is gaining interest as a bone resorption marker (Norio Fukunaga, Toshitaka Nakamura and Toshio Matsumoto, "Osseous Metabolism Marker", Medical Review Co., Ltd., 1995), and it has been found that besides this enzyme having enzymatic activity, fragment as degradation products of the enzyme are also present in serum (J Bone Miner Res. 15:1337-1345, 2000; and Clin Chem. 47:74-80. 2001).

By the way, acid phosphatase in serum is divided into six bands 0 to 5 from the origin by polyacrylamide gel electrophoresis. Of these, acid phosphatase corresponding to the fifth band is tartrate-resistant and is called Band 5 tartrate resistant acid phosphatase (TRACP 5: tartrate resistant acid phosphatase 5). This acid phosphatase is further divided by electrophoresis into 5a which has a high content of sialic acid bonded to a sugar chain and 5b which has almost no sialic acid bonded to a sugar chain. In addition, 5a is an enzyme derived from platelet or the like and its blood level does not vary, while only the blood level of 5b varies with bone resorption. Therefore, it is considered that 5b is the main body of tartrate resistant acid phosphatase derived from osteoclast. Also in "Clinical Chemistry" (Clin. Chem. 47:1497. 2001), it is recommended that ACP derived from osteoclast should be abbreviated as TRACP 5b. Accordingly, also in the present specification, phosphatase that refers to ACP derived from osteoclast and used as an indication of bone resorption is expressed in the term "TRACP 5b", and tartrate resistant acid phosphatase derived from osteoclast and tartrate resistant acid phosphatase 5b (TRACP 5b ) are considered synonymous with each other. Thus, all of them are expressed in the term "TRACP 5b".

Besides TRACP 5b, acid phosphatase derived from erythrocyte or that derived from platelet is present as ACP in a specimen. That is, when hemolysis is caused by collection of a specimen, acid phosphatase derived from erythrocyte is contained in the specimen. When serum is used as a specimen, platelets are destroyed during blood coagulation in serum preparation, so that acid phosphatase derived from platelet is contained in the specimen. Therefore, conventional methods for assaying TRACP activity do not permit assay of osteoclast-specific TRACP 5b. As a modification of these assay methods, there is known a method in which after a pretreatment comprising incubation of a 5-fold dilution of serum at 37° C. for 1hour, the residual TRACP activity is assayed by the use of p-nitrophenylphosphoric acid (pNPP) as a substrate in the presence of tartaric acid ("Nichidai-Ishi", 49:904-911. 1990; and Clin. Chem. 33:458-462. 1987). This method permits avoidance of the influence of acid phosphatase derived from erythrocyte but does not permit exclusion of the influence of acid phosphatase derived from platelet. In addition, as a more specific activity assay method, there is a TRACP 5b assay method utilizing the difference in sensitivity to fluorine between TRACP 5b and tartrate resistant acid phosphatase derived from erythrocyte or platelet (JP-A-10-37198). This method, however, does not permit exclusion of the influence of TRACP 5a though it permits avoidance of the influence of tartrate resistant acid phosphatase derived from erythrocyte or platelet. Moreover, this method is desired to be further improved in precision because TRACP 5b activity is assayed in this method by subtracting activity not inhibited in the presence of fluorine from the total tartrate resistant acid phosphatase activity.

In immunoassay methods such as the method using a polyclonal antibody of Marius E, Sari L, et al. (J Clin Endocrinol Metab. 71:442-451. 1990; and Clin Chem. 46:1751-1754. 2000) and the method using a monoclonal antibody of Jussi M. Halleen, Heather Bull, et al. (J Bone Miner Res. 13:683-687. 1998; Immunol Lett. 70:143-149. 1999; J Bone Miner Res. 14:464-469. 1999; Clin Chem. 45:2150-2157. 1999; and Clin Chem. 46:1751-1754. 2000), activity corresponding to the whole of Band 5 is assayed, so that the influence of TRACP 5a is not negligible. In addition, the method of Halleen, et al., which is designed to assay TRACP 5b specifically, is more specific for TRACP 5b activity derived from osteoclast but indicates only slight difference between a specimen from a healthy person and a specimen from a patient suffering exacerbated bone resorption. Thus, the sensitivity of TRACP 5b as a bone resorption marker is not sufficient. The low specificity for TRACP 5b of heretofore-prepared polyclonal antibodies and monoclonal antibodies is considered as a cause for the defects described above. Since it has been reported that TRACP contains fragments with no enzymatic activity in a large amount of 10 times the amount of the active enzyme in serum, it is also conjectured that the fragments compete with the intact enzyme in serum, so that the specificity has been low because of a disadvantageous reaction system.

Even in such a case, quantification has heretofore been carried out by an immunoassay method or the like by utilizing an antigen common to the complete substance with enzymatic activity, the intact enzyme, and enzyme degradation products. However, as a result, when an epitope is limited as in the case of a monoclonal antibody, measurable fragments and non-measurable fragments appear owing to degradation. Therefore, it can be speculated that there is, for example, the following problem: even when one and the same target substance is assayed, there is no correlation among the assay results obtained by the use of various kits. In addition, it has also been reported that in the case of TRACP, examples of which have been previously given, the amount of its fragments does not clinically reflect bone resorption (J. Bone Miner. Res., 15:1337-1345, 2000; and Clin. Chem. 47:74-80, 2001). This is considered as a proper example of necessity for the measurement of only the enzyme active form. In such a case, only the enzyme level should be measured by removing the fragments. It is conjectured that in general, the assay of TRACP by an activity measurement method has been not accurate because the inactive fragments compete with the enzyme. Moreover, there has been no fragment-specific antibody for clear separation of protein fragments, so that no means for the separation has been present in itself.

DISCLOSURE OF THE INVENTION

Accurate assay of TRACP explained in the present specification has been impossible for a long period of time though it has been said to have a clinical significance. As reasons for this, the following two reasons are thought of. The first reason is that there has been no antibody having a high specificity for TRACP 5b indicating the activity of osteoclast. The second reason is that protein fragments formed by TRACP enzyme degradation are present in serum in an amount larger than that of the active enzyme.

Therefore, in the present invention, by developing a first antibody having a high binding constant value for TRACP active enzyme and a second antibody which hardly reacts with the enzyme and binds to inactive degradation products of the enzyme and utilizing them in one and the same reaction system, only the enzymatic activity level is accurately assayed while avoiding the effects of the degradation products.

In view of such a problem, the present invention provides an immunoassay method in which a first antibody highly reactive with a target substance to be assayed and a second antibody highly reactive with a competitive substance such as an inactive fragment are used in combination at first to exclude the effects of the competitive substance in the reaction system, whereby the target substance such as an active enzyme is assayed specifically and accurately.

That is, the present invention provides an immunoassay method in which a target substance in a specimen is assayed by the use of two types of antibodies, and which comprises using the two types of the antibodies, i.e., a first antibody and a second antibody which have the following properties: (i) the first antibody has affinity for the target substance and a competitive substance, (ii) the first antibody has a higher affinity for the target substance than for the competitive substance, (iii) the second antibody has a higher affinity for the competitive substance than for the target substance, and (iv) the affinity for the competitive substance of the second antibody is higher than the affinity for the target substance of the first antibody, bonding the target substance and the competitive substance in the specimen to the first antibody and second antibody adsorbed on a carrier, and then measuring the level of the bonded target substance to assay the target substance in said specimen.

Furthermore, the present invention provides a kit for immunoassay of a target substance in a specimen by the use of two types of antibodies, which comprises the two types of the antibodies, i.e., a first antibody and a second antibody which have the following properties: (i) the first antibody has affinity for the target substance and a competitive substance, (ii) the first antibody has a higher affinity for the target substance than for the competitive substance, (iii) the second antibody has a higher affinity for the competitive substance than for the target substance, and (iv) the affinity for the competitive substance of the second antibody is higher than the affinity for the target substance of the first antibody.

BRIEF DESCRIPTION OF THE DRAWINGS

FIG. 1 is a simple diagram showing the results of analysis using Protein Chip System of Cyphergen Biosystems. Inc. From the graphs (1) and (2), it was found that in the case of antibody Trk49, there were four kinds of fragments specifically reactive therewith in the serum of an infant. On the other hand, from the graphs (3) and (4), it was found that in the case of antibody Trk62, there was almost no fragment specifically reactive therewith.

MODE FOR CARRYING OUT THE INVENTION

In the immunoassay method of the present invention, two types of antibodies, i.e., a first antibody and a second antibody are used for assaying a target substance to be assayed in a specimen. The first antibody and the second antibody have the following properties: (i) the first antibody has affinity for the target substance and a competitive substance, (ii) the first antibody has a higher affinity for the target substance than for the competitive substance, (iii) the second antibody has a higher affinity for the competitive substance than for the target substance, and (iv) the affinity for the competitive substance of the second antibody is higher than the affinity for the target substance of the first antibody. Here, the term "competitive substance" means a substance which has antigenicity similar to that of the target substance to be assayed and has such a property that when an antibody against the target substance is prepared, the competitive substance binds to this antibody in competition with the target substance. For example, when the target substance is a protein or an enzyme, the competitive substance includes, for example, fragments of the protein or the enzyme, variants having an amino acid sequence formed by substitution, deletion or addition of an amino acid residue(s) in an amino acid sequence constituting the protein or the enzyme, and modification products obtained by the addition of a phosphoric ester group to the protein or the enzyme or the change of the sugar chain portion of the protein or the enzyme.

In the present invention, typical examples of the target substance to be assayed are intact enzymes. When the target substance is an intact enzyme, typical examples of the competitive substance are substances not having the enzymatic activity, such as products produced by the degradation of the enzyme, i.e., enzyme degradation products.

Each of the first antibody and the second antibody in the present invention may be any of an antiserum, a polyclonal antibody and a monoclonal antibody.

The first antibody and second antibody used in the present invention may be prepared, for example, by immunizing an animal with the target substance to be assayed, as an antigen, fusing splenocytes of the animal with myeloma cells to prepare hybridomas, and selecting two types of monoclonal antibodies having the following properties, as the two types of the antibodies, i.e., the first antibody and the second antibody from various monoclonal antibodies produced by the hybridomas: (i) the first antibody has affinity for the target substance and the competitive substance, (ii) the first antibody has a higher affinity for the target substance than for the competitive substance, (iii) the second antibody has a higher affinity for the competitive substance than for the target substance, and (iv) the affinity for the competitive substance of the second antibody is higher than the affinity for the target substance of the first antibody. In the present invention, the second antibody may be an antibody having affinity for both the target substance and the competitive substance. To obtain the two types of the monoclonal antibodies satisfying the above-mentioned four conditions with respect to the target substance and the competitive substance, the following, for example, is sufficient: the binding properties for the target substance and the competitive substance of the various monoclonal antibodies are measured by ELISA or the like, and on the basis of the measurement result, the two types of the monoclonal antibodies satisfying the above-mentioned four conditions are selected. Alternatively, it is also possible to measure the binding constants for the target substance and the competitive substance of the various monoclonal antibodies according to a well-known method ("Protein•Enzyme Fundamental Experimental Methods", Nankohdo Co., Ltd.) and select the two types of the monoclonal antibodies on the basis of the measurement result. In addition, the two types of the monoclonal antibodies may be selected also by preparing affinity-chromatographic columns using each of the various monoclonal antibodies, and assaying the target substance and the competitive substance adsorbed on the columns.

When each of the two types of the antibodies, i.e., the first antibody and the second antibody is an antiserum or a polyclonal antibody, the following, for example, is possible: an animal is immunized with the target substance to be assayed, under various conditions established by changing an adjuvant or varying immunization conditions, and the binding properties for the target substance and the competitive substance of the antisera or polyclonal antibodies thus obtained are measured by the same method as in the case of the above-mentioned monoclonal antibodies, and the two types of the antibodies satisfying the above-mentioned four conditions are selected.

Typical examples of the two types of the antibodies used in the present invention are two types of monoclonal antibodies usable for assaying TRACP 5b derived from osteoclast. Two types of monoclonal antibodies relating to TRACP 5b and obtained according to the present invention are a first monoclonal antibody which has a still higher reactivity with TRACP 5b than do monoclonal antibodies heretofore reported, and hardly reacts with fragments of TRACP 5b, and a second monoclonal antibody which reacts with the inactive enzyme fragments and hardly reacts with the active enzyme. The utilization of these two types of the antibodies makes possible an immunoassay method specific for TRACP 5b derived from osteoclast which is hardly affected by TRACP 5b inactive fragments and other isozymes in blood (derived from erythrocyte, platelet, neutrophil or macrophage).

By taking the case of these monoclonal antibodies, the two types of the antibodies used in the present invention are explained below in further detail.

The above-mentioned monoclonal antibodies may be obtained by using purified TRACP 5b derived from human osteoclast, as an immunogen. Although in the method described below, immunization is carried out by the use of an antigen obtained from normal osteoclast, not only this antigen but also TRACP 5b of osteoclast tumor or the like may be used as an antigen.

The above-mentioned monoclonal antibodies are produced by hybridomas obtained by immunizing an animal with purified human TRACP 5b as antigen and fusing its cells capable of producing anti-human TRACP 5b antibody with myeloma cells.

The above-mentioned hybridomas may be obtained by the following method. That is, human TRACP 5b obtained in the manner described above is mixed with a well-known adjuvant such as Freund's complete or incomplete adjuvant, aluminum hydroxide adjuvant, pertussis adjuvant or the like to prepare an adjuvant liquid for sensitization, and this liquid is administered to an animal (e.g. a mouse or a rat) subcutaneously in the abdominal cavity or intravenously in the tail, in several portions at intervals of 1 to 3 weeks to immunize the animal. Although the amount of the antigen used for the sensitization is usually chosen in the range of 1 µg to 100 mg, it is preferably about 50 µg in general. Although the number of immunizing operations is generally 2 to 7, various methods are known. Subsequently, antibody-producing cells derived from the spleen or the like are fused with cells having proliferating capability in a test tube, such as myeloma cells or the like. The antibody-producing cells may be obtained from a mouse, a nude mouse or a rat.

As to a method for the above-mentioned fusion, the fusion may be carried out by the use of a poly(ethylene glycol) (PEG) by the method of Köhller and Milstein (Nature. 256, 495. 1975) which is already per se well known. The fusion may be carried out also by the use of Sendai virus or by an electrofusion method.

As to a method for selecting hybridoma capable of producing an antibody capable of recognizing human TRACP 5b, from the fused cells, the selection may be carried out as follows. That is, the hybridoma is selected from colonies formed by cells surviving in HAT medium and HT medium in limiting dilution of the aforesaid fused cells. When an antibody against human TRACP 5b is contained in the supernatant of the culture medium for any of the colonies formed by the fused cells seeded into a 96-well plate or the like, a clone capable of producing a monoclonal antibody against human TRACP 5b may be selected by an ELISA method in which the supernatant is placed on an assay plate having human TRACP 5b immobilized thereon, and after the reaction, a secondary labeled antibody such as an anti-mouse immunoglobulin-HRP labeled antibody is reacted with the above-mentioned antibody. As the labeling substance of the labeled antibody, there may be used enzymes (e.g. alkaline phosphatase), fluorescent substances, radioactive substances and the like besides HRP. Screening of specific antibodies against human TRACP 5b may be conducted by carrying out, as a control, ELISA using an assay plate having only BSA bonded thereto as a blocking agent, simultaneously with the above-mentioned ELISA. That is, a clone is selected which is positive on the plate having human TRACP 5b immobilized thereon and is negative in the ELISA using only BSA.

In addition, the following measurement may be carried out at the same time: an anti-mouse immunoglobulin antibody is seeded on a microtiter plate, the supernatant of the culture medium for the fused cells is added thereto to carry out the reaction, purified TRACP 5b is added thereto to bond the active enzyme and form an immune complex, and the enzymatic activity thus bonded is measured by utilizing a color-producing substrate such as pNPP.

The first monoclonal antibody used in the present invention includes monoclonal antibodies capable of specifically recognizing human TRACP 5b which react with, in particular, intact human TRACP 5b, do not undergo cross reaction with acid phosphatase derived from erythrocyte, platelet, neutrophil or prostate and potato ACP, and have a low reactivity with inactive fragments of human TRACP 5b. An example thereof is a monoclonal antibody produced by hybridoma Trk62 established by the present inventor. The second monoclonal antibody used in the present invention includes monoclonal antibodies capable of specifically recognizing human TRACP 5b inactive fragments, which hardly react with, in particular, active human TRACP 5b and do not undergo cross reaction with acid phosphatase derived from erythrocyte, platelet, neutrophil or prostate and potato ACP. An example thereof is a monoclonal antibody produced by hybridoma Trk49 established by the present inventor.

In particular, the first antibody used in the present invention is preferably an antibody having a higher affinity for active human TRACP 5b than for inactive human TRACP 5b fragments, for the purpose of specifically bonding the active enzyme. Especially preferable example thereof is an antibody having a larger binding constant for active human TRACP 5b than does the second antibody. As the second antibody, suitable is an antibody having a binding constant for the inactive TRACP 5b fragments which is larger than the binding constant for active human TRACP 5b of the first antibody. As the first antibody, a monoclonal antibody produced by hybridoma Trk62 established by the present inventor is exemplified. As the second antibody, a monoclonal antibody produced by hybridoma Trk49 established by the present inventor is exemplified. The above-mentioned hybridomas Trk49 and Trk62 were deposited as follows in Patented Organism Deposition Center (IPOD), Industrial Technology General Research Institute (Independent Administrative Corporation), Chuo-dairoku, Higashi 1-1-1, Tsukuba City, Ibaraki Prefecture, Japan 305-8566: hybridoma Trk49 was deposited as a receipt number IPOD FERM BP-8249 on Nov. 27, 2002 and hybridoma Trk62 was deposited as a receipt number IPOD FERM BP-7890 on Feb. 14. 2002.

Each of the above-mentioned hybridomas is cultured on a medium usually used for cell culture, such as α-MEM, RPMI1640, ASF, S-clone or the like, and the monoclonal antibody may be recovered from the supernatant of the culture medium. The following is also possible: after a nude mouse, an animal from which the hybridoma has been derived, is previously treated with pristane, cells are intraperitoneally injected into the animal to cause accumulation of ascites, and the monoclonal antibody is recovered from the ascites.

As a method for recovering the monoclonal antibody from the above-mentioned supernatant or ascites, a conventional method may be adopted. There are exemplified salting-out with ammonium sulfate, sodium sulfate or the like, chromatography, ion exchange chromatography, and affinity chromatography using protein A.

By the use of the monoclonal antibodies according to the present invention purified by the above method, TRACP 5b in a serum specimen can be accurately assayed. The immunoassay method of the present invention is explained below.

The immunoassay method of the present invention may be practiced, for example, as follows. At first, the first antibody and the second antibody are adsorbed on an insoluble solid support such as a plate, and the immunoassay method may be practiced by the same procedure as in a conventional ELISA method except for the above adsorption. A specimen to be subjected to assay is first added to the support having two types of the antibodies adsorbed thereon. In this case, a competitive substance in the specimen undergoes antigen-antibody reaction mainly with the second antibody adsorbed on the support because of the difference in binding constant between the first antibody and the second antibody, and then a target substance in the specimen advantageously undergo antigen-antibody reaction mainly with the first antibody adsorbed on the support. Subsequently, the solid support is washed when occasion demands, and then the level of the target substance attached to the solid support is measured, whereby the target substance in the specimen may be assayed. In this case, when the target substance is an intact enzyme such as TRACP 5b, a solution of a substrate corresponding thereto such as pNPP (p-nitrophenylphosphoric acid) is added to the solid support to carry out the enzyme reaction and measure the level of the target substance attached to the solid plate, whereby the target substance in the specimen can be accurately assayed.

In the present invention, a carrier on which the first antibody is adsorbed may be an insoluble solid support and the second antibody may be adsorbed on a carrier dispersible in a solution, such as a latex or may be dissolved. In this case, a target substance may be assayed as follows. At first, the carrier dispersible in a solution, such as a latex is sensitized with the second antibody or the second antibody is dissolved. On the other hand, the first antibody is adsorbed on the solid support. Then, a solution containing the thus treated second antibody and a specimen to be subjected to assay are added to the solid support, whereby a competitive substance in the specimen is subjected to antigen-antibody reaction mainly with the second antibody and the target substance is subjected to antigen-antibody reaction mainly with the first antibody. Subsequently, the solid support is washed when occasion demands, and then the level of the target substance attached to the solid support is measured, whereby the target substance in the specimen may be assayed. In this case, when the target substance is an intact enzyme such as TRACP 5b, a solution of a substrate corresponding thereto such as pNPP (p-nitrophenylphosphoric acid) is added to the solid support to assay the target substance attached to the solid support, whereby the target substance in the specimen can be accurately assayed.

As explained above, a carrier on which the first antibody is adsorbed is usually an insoluble solid support. The second antibody is used after being adsorbed on the insoluble solid support, or dispersed in a solution containing a latex or the like, or dissolved.

The insoluble solid support is not limited so long as it is one which is used in a solid phase immunoassay method such as ELISA. The insoluble solid support includes, for example, those made of any of polystyrenes, polypropylenes, polycarbonates, polyethylenes, nylons, polymethacrylates and the like. The monoclonal antibody (antibodies) according to the present invention is directly or indirectly bonded to any of the above-exemplified per se well-known solid supports by utilizing physical bonding, chemical bonding or affinity. The amount of the antibody (antibodies) used for the sensitization is often in the range of 1 ng to 100 mg/ml. A specimen to be subjected to assay of human TRACP 5b is added to the monoclonal antibody (antibodies) bonded to the solid support by physical bonding, chemical bonding or affinity, to carry out the reaction. After a definite period of the reaction, the solid support is washed and a color-producing substrate is added thereto to carry out the reaction. As the substrate, a known substrate such as pNPP may be used.

As the carrier dispersible in a solution on which the second antibody is adsorbed, latex particles, magnetic particles and lipid particles may be exemplified. In addition, there may also be used a dispersion obtained by bonding the second antibody to a chemical synthetic polymer, a natural polymer (e.g. a dextran) or the like and dispersing the thus treated polymer in a solution. In this case, the assay of a target substance on a solid plate may be made advantageous by adding the second antibody capable of binding to a competitive substance to a buffer solution reagent in an ELISA method. The assay of a target substance may be made advantageous by bonding the second antibody to an insolubilized carrier and allowing the thus treated second antibody to compete with the first antibody adsorbed on a solid plate. In addition, the assay of a target substance may be made advantageous by bonding the second antibody to a chemical synthetic polymer, a natural polymer (e.g. a dextran) or the like and adding the thus treated antibody to a buffer solution reagent.

The kit for practicing the immunoassay method of the present invention comprises two types of antibodies, i.e., the above-mentioned first antibody and second antibody. As described above, these antibodies may, if necessary, be adsorbed on an insoluble solid support or a carrier dispersible in a solution, such as a latex. If necessary, the kit may further comprises a reagent for assaying a target substance bonded to the antibodies.

As to the present invention, as described in detail hereinafter in Example 1, TRACP 5b fragments in various sera were investigated in practice by the protein chip technology by using monoclonal antibodies Trk49 and Trk62 produced by the above-mentioned hybridomas Trk49 and Trk62, respectively. As a result, it was proved that fragments of TRACP 5b having a molecular weight of about 5580 Da, 5795 Da, 6860 Da or 7075 Da were found in the sera of infants or the sera of patients with osteoporosis, in which bone resorption was actively in progress. Therefore, it was found that these fragments of TRACP 5b are usable as marker molecules for diagnosing bone diseases such as a bone disease in which bone resorption is actively in progress. Accordingly, the bone disease may be diagnosed by detecting these marker molecules in a specimen (e.g. serum, plasma or blood) obtained from a patient, or measuring the amount of these marker molecules.

All methods known at present may be adopted for detecting or quantifying the marker molecules. The methods include, for example, a mass spectrometry method, immunoassay method, electrophoresis method, liquid chromatography method and gas chromatography method. As the mass spectrometry method, a method using a laser desorption/ionization-time of flight-mass spectrometer (LDI-TOF MS) is exemplified. As the laser desorption/ionization-time of flight-mass spectrometer, there may be exemplified surface enhanced laser desorption/ionization-time of flight-mass spectrometers (SELDI-TOF MS method) and matrix-assisted laser desorption/ionization-time of flight-mass spectrometers (MALDI-TOF MS method). For example, when SELDI-TOF MS method is adopted, Protein•Biology•System II•Mass•Spectrometer (Ciphergen Biosystems, Inc.) developed by Ciphergen Biosystems, Inc. may be used. This machine is based on a protein chip technology comprising a combination of SELDI (surface enhanced laser desorption ionization) and a time-of-flight mass spectrometer. The details of the machine are disclosed in International Publication No. WO 01/25791 A2, JP-A-2001-281222 and the like. Usually, in SELDI-TOF MS method, a specimen is pretreated, adsorbed on a chip and then loaded on a SELDI-TOF MS mass spectrometer. When the specimen is serum, it is preferable to remove albumin from the system by using an adsorbent for albumin or washing the system with a buffer solution until the possession of electric charge by albumin owing to the ion exchange chip is ceased. The protein chip used in such a method is not particularly limited so long as it can adsorb the above-mentioned marker molecules. As the protein chip, there may be exemplified chips (referred to also as chemical chips) in which functional groups having affinity for proteins have been modified to give hydrophobicity, ion-exchange properties or the like, and chips (biochemical chips) having an antibody against a protein of interest immobilized thereon.

As another mass spectrometry method, a mass spectrometry method using an ESI method (electrospray ionization) is exemplified. In the case of the ESI method, it is often preferable to load a specimen subjected to pretreatment such as protease treatment, on a mass spectrometer connected directly to a separating means such as high performance liquid chromatography. As the immunoassay method, there may be exemplified a method in which a heretofore known protein is assayed by preparing a polyclonal or monoclonal antibody against the marker molecules. Such an immunoassay method includes an enzyme immunoassay method (EIA method), immunoturbidimetry method (TIA method), latex immuno-agglutination method (LATEX method), electro-chemiluminescence method, fluorescence method and the like. An immuno-chromatography method and a method using test paper are also effective. All of these methods are generally known to those skilled in the art and these generally known methods may be adopted as they are.

Besides the methods described above, an electrophoresis method, liquid chromatography (LC) method, gas chromatography (GC) method and the like are exemplified. These methods are also generally known to those skilled in the art and the measurement can be carried out by adopting these generally known methods as they are.

The present invention is more concretely illustrated with reference to the following preferable working example, which should not be construed as limiting the scope of the invention.

EXAMPLE 1

(1) Selection and Preparation of an Antigen for Preparing Monoclonal Antibodies

TRACP 5b derived from human osteoclast was prepared as an antigen for preparing anti-human TRACP monoclonal antibodies. A purification method is described below.

After informed consent was obtained, 130 g of the caput of human thighbone excised by a surgical operation was frozen in liquid nitrogen, crushed with a hammer, and then suspended in 200 mL of a buffer solution (50 mM Tris-HCl, 0.3M KCl, 1 mM PMSF, 1 mM EDTA·2Na, 0.1% Triton X-100, 0.02% $NaN_3$, 1 unit/ml aprotinin, pH 7.5) containing a protease inhibitor, followed by homogenization in a ultrasonic homogenizer. The homogenate was stirred overnight at 4° C. and centrifuged at 10,000 rpm for 20 minutes, and the supernatant was dialyzed against 10 mM Tris buffer (pH 8.2).

Thereafter, the dialyzed solution was applied to a CM-Sepharose column (Φ40 mm×40 cm) (SIGMA) and the protein adsorbed was eluted with the same Tris buffer as above containing NaCl, while increasing the NaCl concentration with a linear gradient (0-0.5M NaCl). Tartrate resistant acid phosphatase activity was assayed with a substrate p-nitrophenylphosphoric acid, and fractions containing a high level of the activity were pooled. The solution thus obtained was concentrated and then dialyzed against 20 mM Tris buffer (pH 7.2) containing 0.7 M NaCl, and the dialyzed solution was applied to a Superdex 200 column (Φ6 mm×60 cm) (Amersham Pharmacia Biotech). In the same manner as above, tartrate resistant acid phosphatase activity in fractions obtained by elution was assayed and fractions containing the activity were pooled. The solution thus obtained was diluted 2-fold with 20 mM Tris buffer (pH 7.2) and applied to a HiTrap Heparin HP column (5 mL) (Amersham Pharmacia Biotech), and the protein adsorbed was eluted with the same 20 mM Tris buffer (pH 7.4) as above containing NaCl, while increasing the NaCl concentration with a linear gradient (0.35-1M NaCl). Fractions containing a high tartrate resistant acid phosphatase activity were pooled and then concentrated to obtain 0.4 mg of purified acid phosphatase derived from osteoclast.

The amount of the protein was confirmed by $A_{280}$. As to the purity, SDS-PAGE (TIFCO) was carried out, followed by silver staining. As a result, the purity was confirmed by the appearance of a single band at a molecular weight of about 35,000. The enzyme corresponding to the single band was considered as purified TRACP 5b and was used as an immunizing antigen.

(2) Immunization

The purified tartrate resistant acid phosphatase derived from osteoclast (TRACP 5b ) was diluted to a concentration of 250 μg/ml with 50 mM citrate buffer (pH 5.5), and 25 μg (100 μl) of the dilution was thoroughly mixed with 100 μl of Freund's complete adjuvant (WAKO) until emulsification was effected. The suspension thus prepared was intraperitoneally administered to a Balb/c female mouse aged 6 weeks (Nippon Clear Co., Ltd.) under anesthesia with diethyl ether. After 2 weeks, the same amount as above of TRACP 5b (25 μg/ml) was mixed with Freund's incomplete adjuvant (WAKO). By exactly the same operation as in the case of the Freund's complete adjuvant, emulsification was effected to obtain a suspension and the mouse was sensitized with the suspension. Two weeks after this procedure, the same procedure as above was carried out. For the fourth immunization, i.e., final immunization, a dilution of TRACP 5b (25 μg/ml) with 50 mM citrate buffer (pH 5.5) was prepared and then administered to the mouse by injection into the tail vein.

(3) Establishment of Hybridomas

Three days after the final immunization, the spleen was surgically removed from the mouse sensitized with TRACP 5b, under anesthesia with diethyl ether, and was aseptically dispersed to prepare splenocytes. Fusion was carried out according to the method of Köhller and Milstein (Nature, 256, 495, 1975). The splenocytes were fused with myeloma cells P3-X63-Ag8-U1 (P3U1) by the use of a poly(ethylene glycol) (PEG4000) (MERK). As to the fusion ratio, the number of the splenocytes was $8 \times 10^7$, while the number of the myeloma cells P3-X63-Ag8-U1 (P3U1) was $2 \times 10^7$. That is, the fusion ratio of the splenocytes to the myeloma cells was 4:1. The fused cells were dispersed in 10% FCS (INVITROGEN) α-MEM (IRVINE) HAT (Cosmo Bio Co., Ltd.) medium, seeded into a 96-wells microtiter culture plate (Sumitomo Bakelite Co., Ltd.) and then cultured under conditions of 37° C. and 5% $CO_2$.

(4) Screening

After about 2 weeks, the growth of colonies was confirmed and screening was conducted. A method for conducting the screening is described below.

For producing a plate for the screening, TRACP 5b purified in the above item (1) was dissolved in 50 mM citrate buffer and applied into a 96-well plate (Nunc) in an amount of 0.5 μg/100 μl/well. The plate was allowed to stand at 4° C. for two nights and then washed three times with Tris buffer containing 0.05% Tween 20. Each well was applied with 200 μl of 1.5% BSA solution in order to inhibit a nonspecific reaction, and the plate was allowed to stand overnight at 4° C. After the thus completed plate was washed three times with Tris buffer containing 0.05% Tween 20, 100 μl of the culture supernatant was reacted in each well and the plate was further washed. Then, HRP-labeled anti-mouse immunoglobulin antibody (Zymed), a secondary antibody was added to carry out the reaction. After washing, 100 μl of a 3 mg/ml color-producing solution of o-phenylenediamine (OPD) (Nakalai), a color-producing substrate for HRP, in citric acid was added to each well to cause coloration for a definite period. Then, 100 μl of 1N sulfuric acid was added to each well as a terminating solution and absorbance was measured at a measuring wavelength of 492 nm. Clones found to be positive by the above procedure were subjected to recloning by a limiting dilution method, and the supernatants thus obtained were checked again.

(5) Confirmation of Antibodies

The reactivity of clones Trk49 and Trk62 with purified TRACP 5b was confirmed by ELISA to find that clones Trk49 and Trk62 reacted with the plate with high sensitivity though they were different in affinity. As a result, clones Trk49 and Trk62 were selected as clones which had recognized TRACP 5b. Antibodies produced by these clones were assayed by the use of a monoclonal antibody typing kit (Amersham Pharmacia Biotech) to obtain the results shown in Table 1 below.

TABLE 1

| Characteristics of the clones | | |
|---|---|---|
| | Class | Light chain |
| clone Trk49 | IgG1 | κ |
| clone Trk62 | IgG1 | κ |

(6) Preparation and Purification of Monoclonal Antibodies

To a Balb/c female mouse aged 10 weeks (Nippon Clear Co., Ltd.) two weeks after administration of 0.5 ml of pristane (Aldrich) to the mouse were intraperitoneally administered $1 \times 10^7$ cells of each of the hybridomas Trk49 and Trk62 obtained in the above item (5). After about 2 weeks, ascites accumulated in the abdominal cavity of the mouse was surgically collected under anesthesia with diethyl ether. As a result of confirmation by the use of the ascites stepwise diluted as a sample and by the ELISA method adopted for the screening in the above item (4), it was found that the ascites contained a high concentration of a monoclonal antibody. The ascites was treated with 40% ammonium sulfate and dialyzed against PBS, and then the monoclonal antibody was purified by the use of a protein G column (Amersham Pharmacia Biotech) and confirmed by SDS-PAGE. As a result, in the case of both monoclonal antibodies Trk49 and Trk62, a single band was confirmed at a molecular weight of about 150,000 when the antibodies were in a non-reduced state, and two bands were confirmed at molecular weights of about 50,000 and 25,000 when the antibodies had been reduced with mercaptoethanol. The amount of each of the purified antibodies Trk49 and Trk62 was about 15 mg or more per mouse, namely, it was sufficient for industrial utilization.

(7) Assay of Specificity

In order to investigate the specificity of monoclonal antibodies Trk49 and Trk62, the following experiment was carried out by using various isoforms (TRACP 5b, erythrocyte, platelet, PAP (SIGMA), and potato ACP (SIGMA)). A measuring method is briefly as follow.

Each of the monoclonal antibodies purified by the use of Protein G was applied into a solid plate (Nunc) in an amount of 2 μg/well, and the plate was allowed to stand at 4° C. for two days. The plate was washed three times with a 20 mM Tris (pH 7.0) washing solution containing 0.05% Tween 20, and then 200 μL of 1.5% BSA Tris (pH 7.0) was added to each well, followed by overnight blocking at 4° C. The plate thus produced was washed once with the same washing solution as above, and the enzymatic activity of all of the various isoforms was adjusted to 10 IU/L and 100 μl of each of the solutions thus obtained was added to each well of the antibody-attached plate. The reaction was carried out at room temperature for 2 hours. After completion of the reaction, the plate was washed three times with the same washing solution as above and 100 μl of a substrate for acid phosphatase was added, and the reaction was carried out at 37° C. for 1 hour. The enzyme level in each sample was determined from the coloration of the substrate caused by the enzyme captured by the antibody. The measurement was carried out at a photometry wavelength of 405 nm after the addition of 50 μl of a reaction-terminating solution.

As a result, monoclonal antibodies Trk49 and Trk62 were found to have a very high specificity because they reacted only with TRACP 5b and had no cross reactivity with the other isoforms.

(8) Confirmation of Fragments Utilizing a SELDI Method

In recent years, the protein chip technology comprising a combination of surface enhanced laser desorption ionization (SELDI) and a time-of-flight mass spectrometer has been developed by Ciphergen Biosystems Inc., USA and has been begun to be clinically utilized, for example, for the detection of a novel tumor marker. The present inventors tried to capture TRACP 5b fragments in serum in practice by employing said technology and utilizing the monoclonal antibodies produced by the established hybridomas Trk49 and Trk62.

1) Experiment Using PS20 Chips

At first, the present inventors searched for TRACP 5b or its fragments in serum, which were reactive with antibodies Trk49 and Trk62, by the use of PS20 Protein Chip Arrays (Ciphergen Biosystems, Inc). The PS20 chip refers to an antibody-bonding chip and has the following characteristic: a reactive substance in a specimen is first bonded to an antibody bonded to a metal surface, and the substance reacted with the antibody is dissociated from the antibody with a laser and flies in a vacuum, whereby the amount and molecular weight of the substance are determined. A method for experimental operation of the protein chip arrays is briefly described below. At first, hybridomas Trk49 and Trk62 acclimatized to a synthetic medium S-clone (Sanko Junyaku Co., Ltd.) were cultured and each of the antibodies produced by them was purified by the use of Protein G column (Amersham Pharmacia). The concentration of each antibody was adjusted to 500 μg/mL and 2 μL of the solution thus obtained was applied to the PS20 chip.

After the reaction was carried out at room temperature for 1 hour, 5 μL of blocking buffer (1M ethanolamine PBS pH 8.0) (WAKO) was added and the reaction was carried out at room temperature for 10 minutes. After the blocking, the chip was washed with 8 mL of washing buffer (0.5% Triton 100 PBS) at room temperature for 5 minutes. This washing was repeated twice and then the chip was lightly rinsed with PBS. The vicinities of the reaction spots were lightly wiped and 3 μL of each of four samples, i.e., the serum of a healthy volunteer, the serum of an infant aged 12 years or less, the serum of a patient with osteoporosis before hormone substitution therapy and the serum of the patient with osteoporosis after hormone substitution therapy, was applied to the chip. The reaction was carried out overnight at 4° C. After completion of the reaction, the sample was absorbed by Kimwipe (Jujo Kimberley) and the chip was washed with 8 mL of washing buffer (0.5% Triton 100 PBS) at room temperature for 5 minutes. This washing was repeated twice and then the chip was lightly rinsed with PBS. Drops of water were wiped from the chip with Kimwipe (Jujo Kimberley) and 0.5 μL of a saturated sinapic acid (Ciphergen Biosystems Inc)/50% acetonitrile (Wako)/0.5% TFA (Wako) solution was added twice. The thus produced protein chip array was read with Protein•Biology•System II•Mass•Spectrometer (Ciphergen Biosystems, Inc).

2) Results of the Experiment Using PS20 Chips

Figure 1:
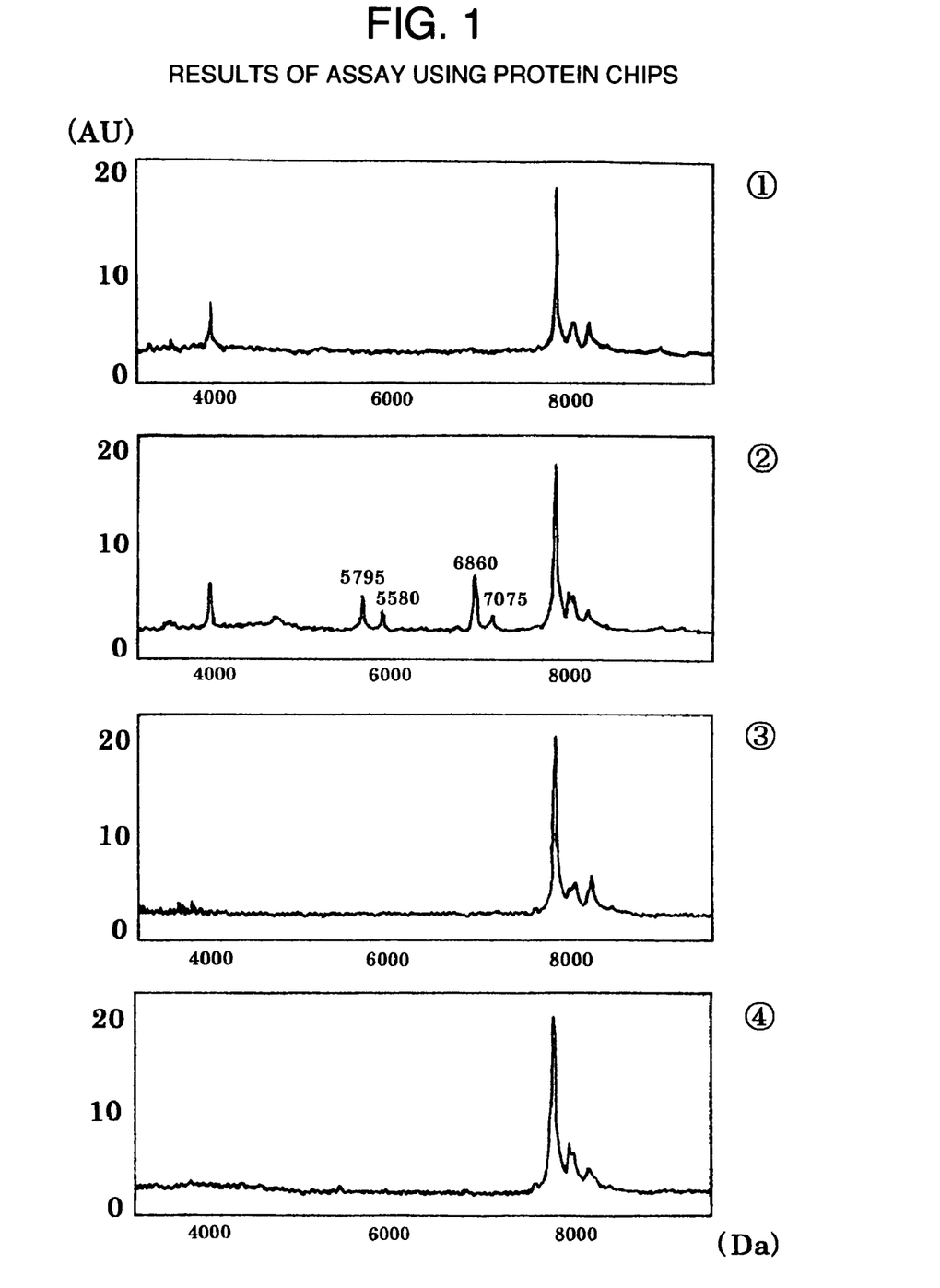
Figure 2:
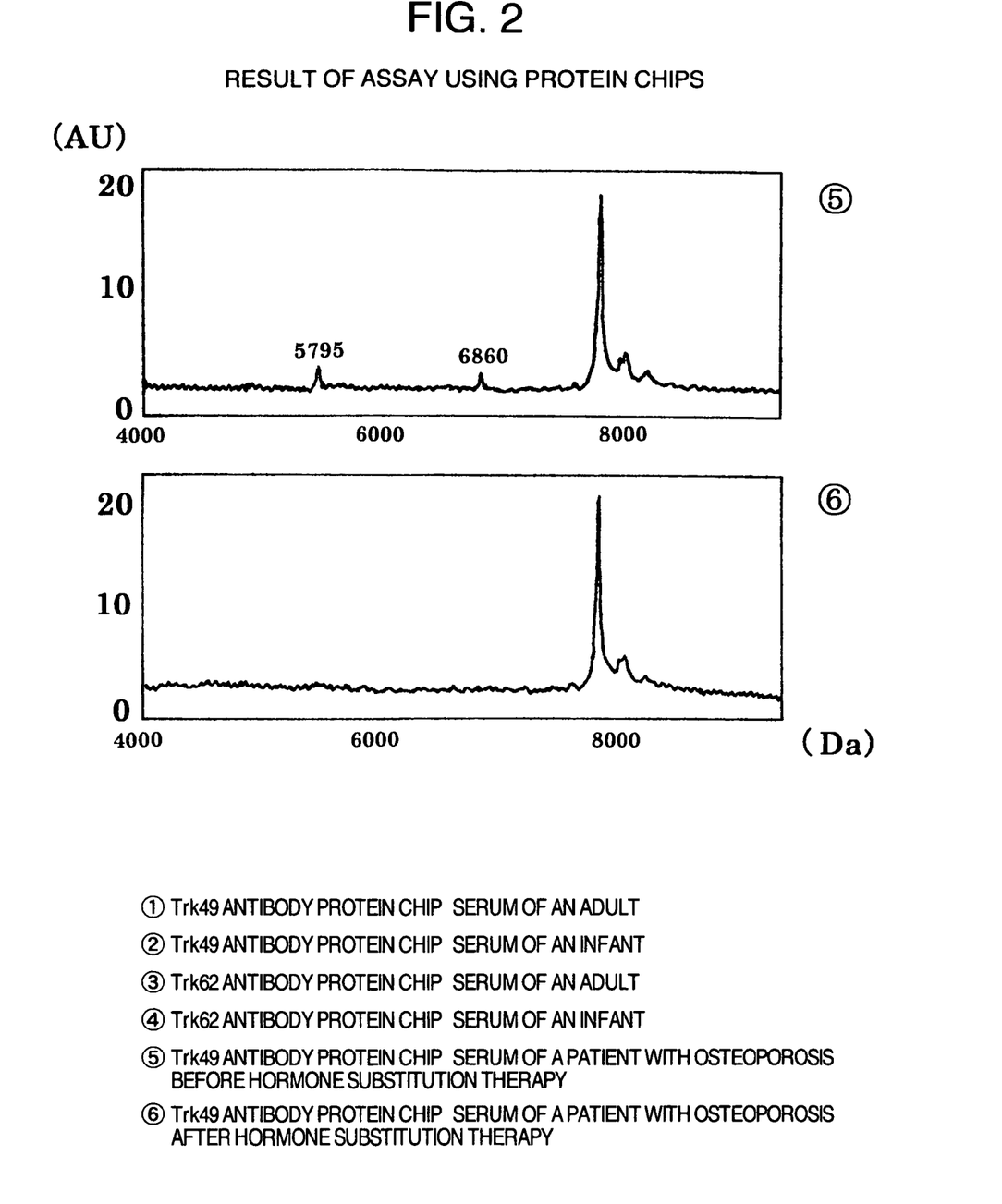
FIG. 2 shows the result of assaying the sera of patients with osteoporosis before and after hormonotherapy. The two peaks observed before this treatment are not present after the treatment. Also from this fact, it is conjectured that fragments corresponding to the two peaks are specific for bone resorption.

Measurement data are shown in FIG. 1 and FIG. 2. In this data format, the axis of abscissa may refer to the molecular weight of a protein in each sample detached from the PS20 protein chip and the axis of ordinate may refer to peak height reflecting the amount of an analyte which arrived at a detector at the aforesaid molecular weight. In this case, unit on the axis of ordinate is arbitrary units (AU). In the experiment described above, the sera of infants and the sera of patients with osteoporosis before hormone substitution therapy are sera in which bone resorption is actively in progress. As a result of the experiment, a peak near 5795 Da and a peak near 6860 Da were observed in the case of the above two experimental groups only when the experiment was carried out using antibody Trk49 (FIG. 1, (2) and FIG. 2, (5)). These peaks were not observed in the case of the sera of adults in which bone resorption was mildly in progress (FIG. 1, (1) and (3)). In the case of the sera of the infants which showed the high peaks, a peak near 5580 Da and a peak near 7075 Da can also be confirmed besides the high peaks (FIG. 1, (2)). The peaks near 5795 Da and near 6860 Da in the case of the patients with osteoporosis disappeared after the treatment by a hormone substitution therapy (FIG. 2, (6)). The reason why the word "near" is used for expressing the molecular weight corresponding to each peak is that there is usually a measurement error of 20 or less. In addition, when the experiment was carried out using antibody Trk62, no specific fragment was found in sera in which bone resorption was actively in progress (FIG. 1, (3) and (4)). As a result of the experiment, the present inventor succeeded in finding several kinds of quite novel TRACP 5b fragments which had been not known. In practice, the fragments are proteins or degradation products thereof, which are detected at about 5795 Da, about 5580 Da, about 6860 Da and about 7075 Da. These fragments are quite novel substances and are markers capable of reflecting bone resorption or morbidity. The amount of the fragments bonded correlates closely with the binding constant of each antibody. Special attention should be paid to the reactivity of antibody Trk62. Antibody Trk62 hardly reacted with fragments to which antibody Trk49 bound, namely, it was proved that antibody Trk62 has a high specificity for the active enzyme. By contrast, antibody Trk49 reacted very well with the fragments. From these facts, the following is conjectured: two types of the monoclonal antibodies used in the present invention, i.e., antibodies Trk49 and Trk62 have a high specificity for the fragments and the enzyme, respectively, so that in the present invention, TRACP 5b can be assayed specifically with high sensitivity by an enzyme immunoassay method using the two antibodies.

(9) Measurement of the Binding Constant of the Monoclonal Antibodies

The following experiment was carried out for determining the binding constant for each of antigens. As to a method for the determination, the determination was carried out according to "Protein•Enxyme Fundamental Experimental Methods", Nankohdo Co., Ltd. Solutions of two kinds of antigens, i.e., (A) purified TRACP 5b and (B) TRACP 5b fragment purified by the use of a Trk49 affinity column (a mixture of fragments of TRACP 5b, comprising at least fragments of TRACP 5b having molecular weights of approximately 5580 Da, 5795 Da, 6860 Da and 7075 Da, respectively) were prepared so as to have a concentration of 5 µg/mL 20 mM citrate buffer. Each well of a 96-well plate (Nunc) was sensitized with 50 µL of each antigen solution. After overnight standing at 4° C., each well of the plate was washed three times with 200 µL of 20 mM Tris buffer containing 0.05% Tween 20, and 100 µL of a blocking agent (20 mM Tris buffer containing 1.5% BSA and 10% saccharose) was added to each well, followed by overnight standing at 4° C. Each well of the plate was again washed three times with 200 µL of 20 mM Tris buffer containing 0.05% Tween 20, and 20 µL of each of antibody solutions obtained by stepwise dilution of each antibody to 12 concentrations (0, 0.1, 0.15, 0.20, 0.25, 0.3, 0.35, 0.4, 0.45, 0.5, 0.75, 1.0 µg/mL) was added to each well. The reaction was carried out for 2 hours under each of conditions (i) 37° C. and (ii) 4° C. After this primary reaction, each well of the plate was washed three times with 200 µL of 20 mM Tris buffer containing 0.05% Tween 20, and 50 µL of a 1000-fold diluted secondary antibody (anti-mouse IgG-HRP labeled antibody: Zymed) was added to each well. The reaction was carried out at 37° C. for 2 hours and each well of the plate was washed three times with 200 µL of 20 mM Tris buffer containing 0.05% Tween 20. Then, 100 µL of a 3 mg/mL OPD solution was added to each well to cause coloration. The coloration was terminated with 100 µL of a 0.1N sulfuric acid solution, followed by colorimetry at 492 nm.

From the results thus obtained, the amount of the monoclonal antibody bonded is determined at first as $A_{492}$ per 1M concentration under the condition (i). For example, since $A_{492}$ was 0.250 when the amount of the antibody on the TRACP 5b plate was 0.05 µg, the amount of the antibody bonded may be determined as follows when the molecular weight of the antibody is taken as 146,000:

$$0.25/\{0.05/(0.146\times10^{-9})\}=0.731\times10^{-9} \quad (1)$$

Next, the concentration of the antibody bonded [PL] at each antibody concentration under the condition (ii) is determined from the value obtained under the condition (i).

$$[PL]=A_{492} \text{ under condition (ii)}/A_{492} \text{ per 1M concentration} \quad (2)$$

Then, the concentration of free antibody [PF] is determined from the concentration of the antibody added.

$$[PF]=\text{the concentration of the antibody added}-[PL] \quad (3)$$

[PL]/[PF] is plotted against the concentration of the antibody bonded and the binding constant (Ka) is determined from the slope (−nK) of the plot.

$$Ka=-\text{slope}/n \quad (4)$$

As a result of the determination by the above method, it was found that the binding constant (ka) values of the two monoclonal antibodies Trk49 and Trk62 were as shown in Table 2 below.

TABLE 2

| Binding constant of the monoclonal antibodies | | |
|---|---|---|
| | Monoclonal antibody | Binding constant |
| Trk49 | (TRACP 5b) | $Ka = 0.94 \times 10^9$ |
| | (TRACP 5b fragment) | $Ka = 5.25 \times 10^9$ |
| Trk62 | (TRACP 5b) | $Ka = 3.73 \times 10^9$ |
| | (TRACP 5b fragment) | $Ka = 0.69 \times 10^9$ |

When the meaning of the above result in the reaction system is figured out, it was found that the activity of reaction, i.e., the affinity is as follows:

The reactivity of Trk49 with the fragment>the reactivity of Trk62 with the enzyme>the reactivity of Trk49 with the enzyme>the reactivity of Trk62 with the fragment Therefore, the following was found: since monoclonal antibody Trk49 has a higher reactivity with the TRACP 5b fragment than with TRACP 5b itself and moreover, this reactivity is higher as compared with the binding constant of monoclonal antibody Trk62 for TRACP 5b, monoclonal antibody Trk49 first binds selectively to the TRACP 5b fragment in the reaction system and monoclonal antibody Trk62 can react with TRACP 5b more advantageously in the reaction system in which the amount of the competitive fragment has been reduced. This result supports the result of the experiment using protein chips.

(10) Measurement Experiment by ELISA

Figure 3:
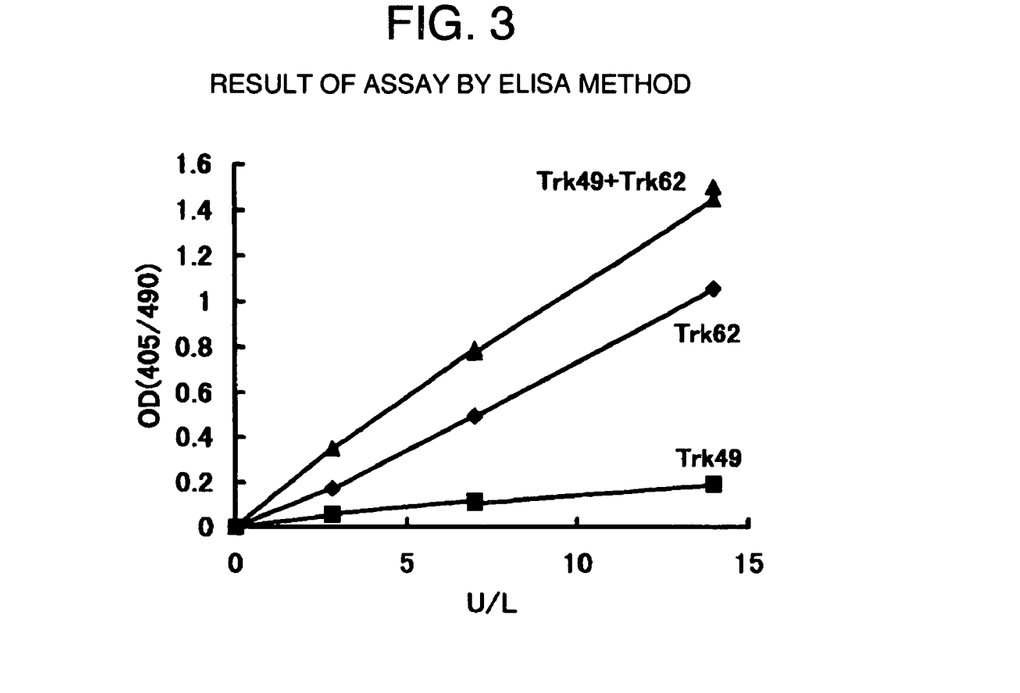
FIG. 3 shows the result of ELISA using the same concentration of antibodies Trk49 and Trk62. Antibody Trk49 exhibited only low reactivity. However, an improved reactivity was exhibited on a plate on which antibodies Trk49 and Trk62 had been used at the same time, as compared with the case of using antibody Trk62 alone.

Therefore, the following five kinds of plates were produced: Trk49 1 µg/well/100 µL, Trk49 2 µg/well/100 µL, Trk62 1 µg/well/100 µL, Trk62 2 µg/well/100 µL, and (Trk49 1 µg +Trk62 1 µg)/well/100 µL. A method for producing the plates was the same as in the production for the assay of specificity of the monoclonal antibodies in the above item (7), except for the following change: the volume of the sensitizing antibody solution 100 µL, the volume of the blocking solution 100 µL, and the volume of a sample 100 µL. As to a primary reaction, pooled serum with a high TRACP 5b level (containing at least fragments of TRACP 5b having molecular weights of approximately 5580 Da, 5795 Da, 6860 Da and 7075 Da, respectively) was added as a sample to the antibody adsorbed on the plate, and the antigen-antibody reaction was carried out with shaking at room temperature. Then, a washing procedure was carried out and 100 µL of a synthetic substrate solution was added to each well, and the enzymatic reaction was carried out at 37° C. for 1 hour. The reaction was terminated by the addition of a 0.2 N NaOH solution, followed by colorimetry, whereby the enzymatic activity was determined. The results obtained are shown in FIG. 3.

Antibody Trk49 supposed to have a low reactivity with the enzyme and a high reactivity with the fragments on the basis of its binding constants had a low avidity for the enzyme and hence gave no sensitivity necessary for the measurement. On the other hand, antibody Trk62 supposed to have a high reactivity with the enzyme on the basis of its binding constant showed a good linearity. Furthermore, in the case of the plate having a mixture of antibody Trk49 and antibody Trk62, a longer linearity and an improved sensitivity were attained. Since the linearity and sensitivity were hardly improved even when the amount of each antibody was increased from 1 µg to 2 µg, it is conjectured that as the amount of each antibody involved in the reaction, 1 µg/well was substantially sufficient. That is, it is conjectured that the linearity and sensitivity were improved because in accordance with the theory based on the binding constant experiment, antibody Trk49 bound to the fragments in the reaction system substantially preferentially and then antibody Trk62 bound to the intact enzyme.

(11) Fragment Absorption Method Using a Latex Reagent

Using monoclonal antibody Trk49 which had been found to be able to absorb the fragments substantially specifically and monoclonal Trk62 as control, a latex was sensitized with each of these two monoclonal antibodies to prepare a latex reagent. The preparation of the latex reagent was carried out as follows.

With 2 mL of a 1% latex suspension was mixed 2 mL of a 0.1 mg/mL solution of each of antibodies Trk49 and Trk62, and the resulting mixture was stirred for about 1 hour. After centrifugation, the precipitate was suspended in a 1% BSA solution and the suspension was re-stirred for about 1 hour. After re-centrifugation, the precipitate was suspended in a PBS solution to obtain a latex reagent. This latex reagent was diluted to 8 concentrations, i.e., 0.15% and 7 concentrations attained by 2-fold dilution from 0.1% (0.1, 0.05, 0.025, 0.0125, 0.00625, 0.00313 and 0.00156%) to prepare 8 latex reagents in total. Operations in an ELISA method are explained below.

Figure 4:
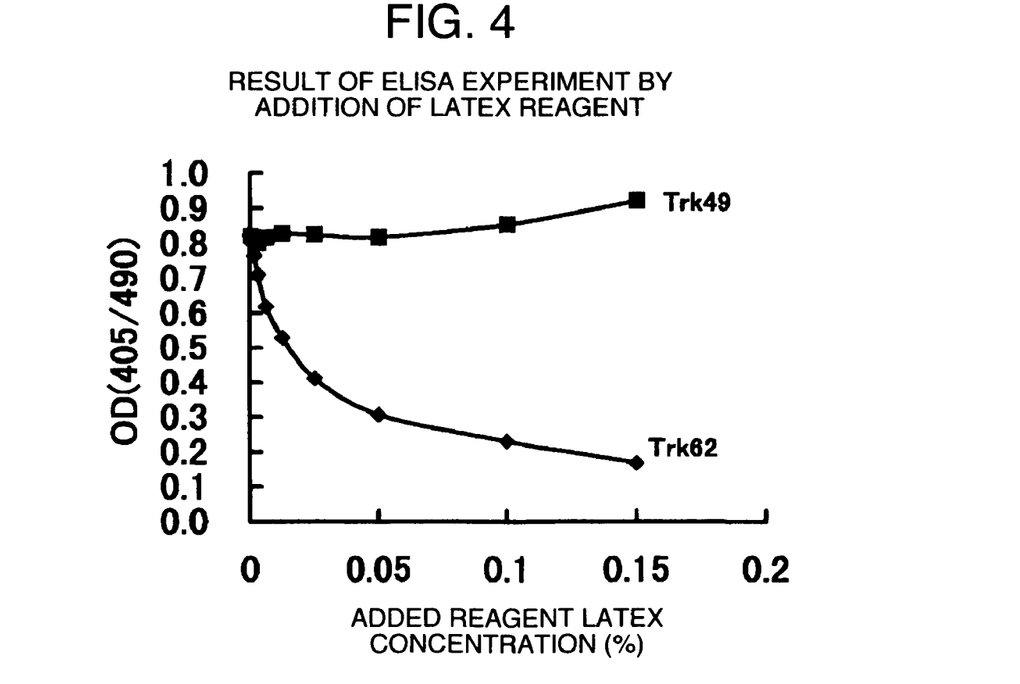
FIG. 4 shows the result of ELISA carried out by adsorbing antibody Trk62 on a plate and adsorbing either antibody Trk62 or Trk49 on latex particles. In the case of the resulting Trk62 antibody-sensitized latex reagent competitive with the plate, coloration was reduced with an increase of the concentration of the latex reagent added. However, by contrast, in the case of the Trk49-sensitized latex reagent, the coloration value of an enzyme was increased in 0.1% to 0.15% experimental groups. Accordingly, it was found that the Trk49 antibody-sensitized latex reagent was effective when used in combination with antibody Trk62 adsorbed on the plate.

At first, 50 µL of each of these latex reagents was applied to each well of a plate seeded with antibody Trk62 (2 µg/well). Then, 100 µL of pooled serum with a high TRACP 5b level (8U/mL) obtained from a patient from whom informed consent had been obtained was added to each well, and the reaction was carried out with shaking at room temperature for 1 hour. After completion of the reaction, the plate was washed three times with 20 mM Tris buffer (pH 7.0) containing 0.05% Tween 20 and a synthetic substrate solution was added thereto. After incubation at 37° C. for 1 hour, 50 µL of a reaction-terminating solution (a 0.2 N NaOH solution) was added to each well, followed by measurement at 405/490 nm. The results obtained are shown in FIG. 4. In the Trk62-sensitized latex reagent addition experiment, competition with the monoclonal antibody on the plate was caused, so that enzymatic coloration was decreased depending on the concentration of the latex reagent added. However, in the case of antibody Trk49, a significantly increased enzymatic coloration value was obtained in the 0.1~0.15% latex reagent addition experiment. This fact, for example, indicates that not only simultaneous sensitization of a plate with the antibodies but also such an absorption method using a carrier for adsorption such as a latex are effective for the absorption of the competitive fragments. In addition, it was also effective to use a solution obtained by dissolving antibody Trk49 in a solution, instead of sensitizing a latex with antibody Trk49.

INDUSTRIAL APPLICABILITY

As explained above in detail, the immunoassay method of the present invention makes it possible to assay a target substance to be assayed such as an active enzyme specifically and accurately by using a combination of a first antibody having a high reactivity with the target substance and a second antibody having a high reactivity with a competitive substance such as an inactive fragment of the target substance, to avoid the effects of the competitive substance in the reaction system.

The invention claimed is:

1. An immunoassay method in which tartrate resistant acid phosphatase 5b (TRACP 5b) is assayed in a specimen containing the tartrate resistant acid phosphatase 5b (TRACP 5b) together with a competitive substance therein, the method comprising:

providing a first antibody that is Trk62 produced by a hybridoma deposited under the Budapest Treaty at National Institute of Advanced Industrial Science and Technology, International Patent Organism Depositary, under the accession number of FERM BP-7890, and a second antibody that is Trk49 produced by a hybridoma deposited under the Budapest Treaty at National Institute of Advanced Industrial Science and Technology, International Patent Organism Depositary, under the accession number of FERM BP-8249, bonding the tartrate resistant acid phosphatase 5b and the competitive substance in the specimen to the first antibody and second antibody, wherein the first antibody and second antibody are both adsorbed on a first carrier, or wherein the first antibody is adsorbed on a first carrier and the second antibody is adsorbed on a second carrier dispersed in a solution or is dissolved in a solution, and then measuring the level of the bonded tartrate resistant acid phosphatase 5b to assay the amount of tartrate resistant acid phosphatase 5b in said specimen, wherein the measurement of the level of the bonded tartrate resistant acid phosphatase 5b is the measurement of the amount of enzymatic activity of the bonded tartrate resistant acid phosphatase 5b, and wherein the competitive substance is a substance not having enzymatic activity of tartrate resistant acid phosphatase 5b.

2. The immunoassay method according to claim 1, wherein the carrier on which at least the first antibody is adsorbed is an insoluble solid support.

3. A kit for immunoassay of a target substance in a specimen by the use of two types of antibodies, which comprises a first antibody that is Trk62 produced by a hybridoma deposited under the Budapest Treaty at National Institute of Advanced Industrial Science and Technology, International Patent Organism Depositary, under the accession number of FERM BP-7890, and a second antibody that is Trk49 produced by a hybridoma deposited under the Budapest Treaty at National Institute of Advanced Industrial Science and Technology, International Patent Organism Depositary, under the accession number of FERM BP-8249, wherein the first antibody and the second antibody are adsorbed on a carrier, or wherein the first antibody is adsorbed on a carrier and the second antibody is adsorbed on a carrier dispersed in a solution or is dissolved in a solution.

* * * * *